(12) United States Patent
Frattarelli et al.

(10) Patent No.: US 8,911,985 B2
(45) Date of Patent: Dec. 16, 2014

(54) ENZYMATIC CONVERSION OF VOLATILE ORGANIC COMPOUNDS

(71) Applicant: Rohm and Haas Company, Philadelphia, PA (US)

(72) Inventors: David L. Frattarelli, Midland, MI (US); Kathleen Rising Manna, Quakertown, PA (US); James Charles Bohling, Lansdale, PA (US); Selvanathan Arumugam, Blue Bell, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 13/892,594

(22) Filed: May 13, 2013

(65) Prior Publication Data

US 2013/0309748 A1  Nov. 21, 2013

Related U.S. Application Data

(60) Provisional application No. 61/646,963, filed on May 15, 2012.

(51) Int. Cl.

| | |
|---|---|
| *C02F 3/34* | (2006.01) |
| *C12N 9/04* | (2006.01) |
| *C08F 6/00* | (2006.01) |
| *C09D 5/02* | (2006.01) |
| *C09D 7/12* | (2006.01) |
| *C08L 25/14* | (2006.01) |

(52) U.S. Cl.
CPC .............. *C12N 9/0006* (2013.01); *C08F 6/006* (2013.01); *C09D 5/024* (2013.01); *C09D 7/125* (2013.01); *C08L 25/14* (2013.01)
USPC ........................................................ 435/262

(58) Field of Classification Search
CPC ...... C12P 7/42; C12N 9/0004; C12N 9/0036; C12N 9/16; C12N 9/0006; C09D 5/14; C09D 5/1625; C09D 7/125; C09D 4/00; C09D 5/1637; C09D 7/1233; C09D 5/008; C09D 5/1606; C09D 5/1687; C09D 7/1291; C08L 33/08; C12Y 101/01274; C12Y 101/01307; C12Y 101/03013; C12Y 103/03006; C12Y 111/01007; C12Y 115/01001; C12Y 101/03004
See application file for complete search history.

(56) References Cited

U.S. PATENT DOCUMENTS

| | | | |
|---|---|---|---|
| 5,292,660 A | 3/1994 | Overbeek et al. | |
| 5,856,150 A | 1/1999 | DiGregorio et al. | |
| 2005/0147579 A1* | 7/2005 | Schneider et al. | ......... 424/78.09 |
| 2009/0022644 A1 | 1/2009 | Sweredjuk | |
| 2010/0022606 A1 | 1/2010 | Tran et al. | |
| 2011/0166257 A1 | 7/2011 | Bohling et al. | |

FOREIGN PATENT DOCUMENTS

| | | |
|---|---|---|
| CN | 101353543 A | 1/2009 |
| EP | 2308934 A2 | 4/2011 |
| WO | WO 2010/089598 A1 * | 8/2010 |

OTHER PUBLICATIONS

Keinan et al., J. Am. Chem. Soc. 108: 162-169 (1986).*
Katchalski-Katzir et al., J. Mol. Catal. B: Enzymatic 10: 157-176 (2000).*
http://web.archive.org/web/20100313074014/http://en.wikipedia.org/wiki/Glucose_oxidase, archived Mar. 13, 2010, accessed Jan. 10, 2014.*
Lamed et al., Biochem. J. 195: 183-190 (1981).*
Moayed et al., Progress in Organic Coatings 60: 312-319 (2007).*

* cited by examiner

*Primary Examiner* — Patricia A Leith
*Assistant Examiner* — Erin M Bowers
(74) *Attorney, Agent, or Firm* — Reid S. Willis

(57) ABSTRACT

The present invention relates to a composition comprising a stable aqueous dispersion of polymer particles, an oxidoreductase, and a cofactor for the oxidoreductase and a method for its preparation. The invention is useful for converting certain classes of VOCs to non-VOCs.

5 Claims, No Drawings

ENZYMATIC CONVERSION OF VOLATILE ORGANIC COMPOUNDS

BACKGROUND OF THE INVENTION

Emulsion polymers are prepared by the polymerization of unsaturated monomers using ionic- or free radical-initiated and propagated reactions. In addition to producing the desired polymer or polymers, the reaction generates detectable levels of unreacted by-products and leaves behind small amounts of unreacted monomer as well as saturated or unsaturated impurities present in the monomer; consequently, post-polymerization small-molecule residuals, in the form of unsaturated monomer, monomer by-products (e.g. saturated esters), and reaction by-products may create odor, instability, or toxicity. Subsequent reduction or elimination of these residual compounds has been disclosed. For example, residual unsaturated esters are known to be polymerized by heating for prolonged periods, with or without the addition of an ion- or a free radical-source; physical removal of residual unsaturated monomer by vacuum stripping and steam sparging is also known, as is conversion to less undesirable species by way of enzymatic hydrolysis.

For most polymers, saturated and unsaturated esters are not the only source of potential odor: Aldehydes, ketones, and alcohols, may each contribute to malodor in compositions, making their removal from the composition desirable or even necessary.

United States Patent No. US 2011/0166257 A1, (Bohling et al.) discloses a method for reducing residual ester levels and aldehydes, in particular, acetaldehyde in coating formulations. Bohling et al. discloses that residual esters and aldehydes can be reduced by treatment with a hydrolytic enzyme, particularly lipase or esterase, in combination with a nitrogen-containing nucleophilic molecule and/or sodium bisulfite. However, this disclosure does not discuss a method to assist in reducing alcohol content during the remediation of esters and aldehyde odorants.

Chinese patent No. CN 101353543A, also discloses enzymes for redox reactions in dry coatings for aldehyde abatement, specifically formaldehyde. However, this disclosure does not teach how to achieve effective aldehyde abatement.

It is therefore an object of this invention to provide stable aqueous polymer compositions with a conversion of VOCs, especially aldehydes and alcohols, to non-VOCs.

SUMMARY OF THE INVENTION

The present invention addresses a need by providing, in one aspect, a composition comprising a stable aqueous dispersion of polymer particles, an oxidoreductase, and a cofactor for the oxidoreductase.

In a second aspect, the present invention is a method comprising the step of contacting a latex containing residual aldehyde or ketone or alcohol VOCs, or combinations thereof, with an oxidoreductase and a cofactor for the oxidoreductase to reduce the concentration of the VOCs in the latex.

The present invention addresses a need by removing residual aldehydes and alcohols from compositions containing these unwanted odor bodies.

DETAILED DESCRIPTION OF THE INVENTION

In a first aspect, the present invention is a composition comprising a stable aqueous dispersion of polymer particles, an oxidoreductase, and a cofactor for the oxidoreductase. The stable aqueous dispersion of polymer particles (also known as a latex) typically has a solids content in the range of from 20 to 65 weight percent and a particle size in the range of from 10 nm to 1 µm. Examples of suitable latexes include acrylic, styrene-acrylic, or vinyl acetate based latexes. The latex, which contains VOCs such as butanaldehyde, benzaldehyde, acetaldehyde, furfural, butanol, benzyl alcohol, ethanol, and acetone, is contacted with an oxidoreductase and a cofactor for the oxidoreductase to substantially reduce the level of these undesirable compounds in the latex. An example of a suitable oxidoreductase is a Group EC1 enzyme in conjunction with a cofactor such as $NADP^+$, NADPH, $NAD^+$, and NADH. Preferably, one or the other of cofactor $NADP^+$ or NADPH is added as a cofactor and converts to some degree to the other during the course of the treatment. For treatment of latexes that contain aldehyde and/or alcohol VOCs, but not ketones, it is preferable to use an oxidizing cofactor such as $NADP^+$ to oxidize the volatile aldehydes and alcohols to the corresponding carboxylic acids and, under basic conditions, to the non-volatile salts of the acids.

VOCs can also be reduced by converting a more volatile VOC to a less volatile VOC. For example, acetone is more volatile than its corresponding reduced alcohol, isopropyl alcohol; in this case, it is preferable to use a reducing cofactor, preferably NADPH, to reduce the more volatile acetone to the less volatile isopropyl alcohol.

The latex, oxidoreductase, and cofactor are typically contacted together at a sufficiently high temperature to promote conversion of the VOCs to non-VOCs without substantial denaturing of the enzyme. Preferably, the reagents are contacted together at a temperature in the range of from ambient temperature, more preferably from 35° C., to 55° C., more preferably to 45° C., and at a pH of from 4, more preferably from 7, to a pH of 10, more preferably to 9.

The concentration of the oxidoreductase is typically in the range of from 10 ppm, more preferably from 30 ppm, to 100 ppm, more preferably to 80 ppm based on the weight of the latex. The preferred ratio of the cofactor to the oxidoreductase varies depending on whether the cofactor is an oxidizing cofactor or a reducing cofactor. When the cofactor is a reducing cofactor such as NADPH and the pH of the latex is from 8 to 10, the ratio of the reducing cofactor to the oxidoreductase is preferably from 0.5:1, more preferably from 0.7:1, and most preferably from 0.8:1, to 5.0:1, more preferably from 2.0:1, and most preferably to 1.0:1. Under similar pH conditions, when the cofactor is an oxidizing cofactor such as $NADP^+$, the ratio of the oxidizing cofactor to the oxidoreductase is preferably from 0.5:1, more preferably from 0.7:1, most preferably from 1.5:1, to 5:1, more preferably to 2.5:1.

The compositions of the present invention may further include a carboxyesterase to hydrolyze saturated and unsaturated carboxyesters, which may be present prior to or after polymerization. The amounts of carboxyesterase are preferably in the range of from 1 ppm, preferably from 10 ppm to preferably 1000 ppm, more preferably to 500 ppm, and most preferably to 200 ppm. If a carboxyesterase is used, the composition may further include an inhibitor for the carboxyesterase, typically from 0.01 weight percent to 1 weight percent, more preferably to 0.1 weight percent, based on the dry weight of the latex. The carboxyesterase and inhibitor, if used, may be contacted with the latex prior to, concurrent with, or subsequent to contact of the oxidoreductase and cofactor with the latex.

The oxidized or reduced forms of the compound(s) have greatly reduced vapor pressures which result in lower "wet in-can" odor.

EXAMPLES

The following examples are for illustrative purposes only and are not intended to limit the scope of the invention.

Materials:

Novozym 51032 Lipase [Novozymes, Bagsvaerd, Denmark] was supplied as a 5% solution; ADH002 aldo-ketoreductase [Codexis, Redwood City, Calif.] was supplied as dry powder.

Bulk Headspace GC-MS VOC Analysis

The samples were analyzed using bulk headspace sampling combined with gas chromatography with mass selective detection (headspace GC-MS). The headspace unit was a Tekmar model 7000. The GC-MS was an Agilent model 6890/5973. For this analysis, the samples were heated to 150° C. for 10 minutes prior to sampling. Samples were prepared by weighing 20-30 mg of each sample into 22-mL headspace vials followed by capping with Teflon-lined septa. Water blanks were run in between each sample.

Calibration standards were prepared at approximately 1 ppm, 10 ppm, 25 ppm, 50 ppm, 100 ppm, 500 ppm and 1000 ppm (weight-to-weight) in either THF or 1-propanol. Standards were prepared by weighing 20-30 mg of each calibration mix into 22-mL headspace vials and capping with Teflon-lined septa. The headspace analysis of the standards was done in a full-evaporation mode to eliminate matrix effects that can occur in static headspace sampling. In this mode, a small sample size was used, and the headspace vial temperature was set sufficiently high to allow for full volatilization of the VOC of interest. For this analysis, the standard samples were heated to 150° C. for 10 min prior to sampling. For each of the compounds requiring calibration, a calibration plot was prepared using at least three standard concentrations for that compound. The amount of each compound was then determined using the linear-least-squares equation from the calibration plot for that compound. An average response factor was used to calibrate any compound in the sample that did not have a calibration standard. Water blanks were run in between each sample.

Enzyme Treatment of Emulsion Polymer Latexes

Known amounts (~15 to 20 mg) of vinyl-acrylic, styrene-acrylic and all acrylic latexes were sampled in separate sealed vials and analyzed by bulk head-space GC-MS for their VOC content prior to the oxidoreductase treatment. In the case of the vinyl-acrylic latex, 0.01 wt % of the carboxyesterase Novozym 51032 Lipase was added 48 h prior to oxidoreductase treatment to convert vinyl acetate completely to acetaldehyde. To 10 g of pre-analyzed latex binder sample, a known amount of ADH002 aldo-ketoreductase (32 to 70 mg) was added followed by the addition of either NADP+ (37-84 mg) or NADPH (45-90 mg) as cofactors.

Enzyme additions were carried out at RT and the containers were tightly sealed and placed over a hot plate pre-heated to 40° C. The samples were continuously stirred for 24 h, with subsequent cooling to RT (Cooling time 10 to 15 min) for GC analysis. A control sample without enzyme was also prepared following the similar procedure to determine the relative change in VOC content. The enzyme/cofactor addition to each sample was delayed by 30 min to match the time differences in GC run series.

Tables 1a and 1b show the effect of enzyme and cofactor on the reduction of aldehyde VOCs (1a) and acetone (1b) doped into an all acrylic latex at time 0. The experiments were carried out at a pH of 8 over 24 h.

TABLE 1a

Conversion of Aldehyde VOCs

| Treatment Conditions | | | | VOC Concentration (ppm)[1] | | | |
|---|---|---|---|---|---|---|---|
| Enzyme | Cofactor | T (° C.) | [Cof]/[Enz] | Acetaldehyde | Benzaldehyde | Butanal | Furfural |
| None | None | 40 | None | 23 | 130 | 43 | 81 |
| None | NADP+ | 40 | 0 | 22 | 123 | 44 | 86 |
| 50 ppm | None | 40 | NA[2] | 19 | 119 | 39 | 78 |
| 50 ppm | NADPH | 25 | 0.9 | 9 | 13 | 8 | 1 |
| 50 ppm | NADPH | 40 | 0.9 | 9 | 4 | 6 | 1 |
| 50 ppm | NADP+ | 50 | .74 | 4 | 2 | 2 | 1 |

[1]Measured by headspace GC-MS at 150° C.;
[2]Not Available.

TABLE 1b

Conversion of Acetone

| Treatment Conditions | | | Acetone (ppm) |
|---|---|---|---|
| Enzyme | Cofactor | T (° C.) | |
| None | None | 40 | 2066 |
| None | NADP+ | 40 | 1726 |
| Yes | None | 40 | 1649 |
| Yes | NADP+ | 40 | 1410 |
| Yes | NADPH | 50 | 1279 |

The results from Table 1a show the significance of the enzyme and the cofactor to the conversion of the aldehyde VOCs. Reactions carried out a 40° C. were found to be optimal because gelation of the latex was observed at 50° C. before completion (24 h). The conversion of acetone, though significant, is not as dramatic.

Table 2 shows the effect conversion of alcohol VOCs to non-VOCs in a non-doped butyl acrylate/methyl methacrylate (BA/MMA) all acrylic system at 40° C. over 24 h.

TABLE 2

Conversion of Alcohol VOCs in BA/MMA Latex

| Treatment Conditions | | | | Alcohol Concentration (ppm) | | | |
|---|---|---|---|---|---|---|---|
| Enzyme (ppm) | Cofactor | pH | [Cof]/[Enz] | 1-Butanol | Methanol | t-Butanol | Ethanol |
| None | None | 8.34 | None | 389 | 305 | 64 | 1052 |
| 70 | NADP+ | 8.34 | 0.88 | 57 | 77 | 12 | 109 |
| 64 | NADPH | 8.34 | 1.4 | 91 | 65 | 13 | 206 |

The results from Table 2 show that both cofactors are effective for the conversion of alcohol VOCs, with the oxidizing cofactor NADP being somewhat more efficient.

Table 3 shows the percent reduction of acetaldehyde, benzaldehyde, and 1-butanol in vinyl-acrylic (VA), styrene-acrylic (SA), and all acrylic (AA) latexes. The concentration of enzyme used ranged from 32 to 70 ppm.

TABLE 3

Percent Removal of Acetaldehyde, Benzaldehyde, and 1-Butanol as a function of pH and Cofactor:Enzyme Ratios

| Cofactor Type | Binder | Treatment Conditions | | Percent (%) Reduction in: | | |
| --- | --- | --- | --- | --- | --- | --- |
| | | [Cof]/[Enz] | pH | Acetaldehyde | Benzaldehyde | 1-Butanol |
| $NADP^+$ | VA | 0.89 | 4.61 | 88 | 19 | 74 |
| NADPH | VA | 1.4 | 4.61 | 94 | 30 | 73 |
| $NADP^+$ | VA | 2 | 4.61 | 94 | 31 | 61 |
| $NADP^+$ | SA | 0.89 | 7.31 | 94 | 94 | 32 |
| NADPH | SA | 1.4 | 7.31 | 96 | 96 | 36 |
| $NADP^+$ | SA | 2 | 7.31 | 94 | 94 | 10 |
| NADPH | SA | 2 | 7.31 | 94 | 94 | −40 |
| $NADP^+$ | AA | 0.74 | 9 | 85 | N.A. | N.A. |
| NADPH | AA | 0.90 | 9 | 91 | N.A. | 87 |
| NADPH | AA | 2 | 9 | 92 | N.A. | 68 |
| $NADP^+$ | AA | 2 | 9 | 93 | N.A. | 81 |

The results show that removal of the VOCs appears to depend on cofactor type, the ratio of cofactor to enzyme, and pH. For example, if the ratio of cofactor to enzyme is too high in the styrene-acrylic latex, the amount of 1-butanol actually increases.

The invention claimed is:

1. A composition comprising:
    A) a latex comprising acrylic polymer particles, styrene-acrylic polymer particles, or vinyl-acrylic polymer particles, wherein the particles have a particle size in the range of 10 nm to 1 μm;
    B) an oxidoreductase; and
    C) a cofactor for the oxidoreductase;
    wherein the composition has a pH of from 8 to 10 and wherein the weight-to-weight ratio of the cofactor to the oxidoreductase is from 0.5:1 to 5:1.
2. The composition of claim 1 wherein the cofactor is $NADP^+$, NADPH, $NAD^+$, or NADH.
3. The composition of claim 2 wherein the cofactor is $NADP^+$ or NADPH.
4. The composition of claim 1 wherein the oxidoreductase is present at a level of from 10 to 100 ppm, and the weight-to-weight ratio of the cofactor for the oxidoreductase to the oxidoreductase is from 0.7:1 to 2.5:1 when the cofactor for the oxidoreductase is an oxidizing cofactor, and from 0.5:1 to 2.0:1 when the cofactor for the oxidoreductase is a reducing cofactor.
5. The composition of claim 4 which further includes a carboxyesterase.

* * * * *